United States Patent [19]

Haber et al.

[11] Patent Number: 5,098,382

[45] Date of Patent: Mar. 24, 1992

[54] SAFETY MODULE-ACTIVATOR RESHIELDING TOOL

[75] Inventors: Terry M. Haber, El Toro; Clark B. Foster, Laguna Niguel; William H. Smedley, Lake Elsinore; John A. Lewis, Jr., Costa Mesa, all of Calif.

[73] Assignee: Habley Medical Technology Corporation, Laguna Hills, Calif.

[21] Appl. No.: 448,292

[22] Filed: Dec. 11, 1989

[51] Int. Cl.$^5$ .............................................. A61M 5/00
[52] U.S. Cl. ..................... 604/110; 604/195; 604/220; 604/232; 604/235
[58] Field of Search ........... 604/198, 195, 197, 110, 604/223, 224, 332, 233, 234, 235, 187, 218, 220, 207–210; 222/325, 326, 327

[56] References Cited

U.S. PATENT DOCUMENTS

| | | | |
|---|---|---|---|
| 1,685,984 | 10/1928 | Cournand et al. | 604/235 |
| 2,118,221 | 5/1938 | Montuori | 604/235 |
| 2,672,868 | 3/1954 | Hickey | 604/234 |
| 2,871,858 | 2/1959 | Darn et al. | 604/233 |
| 3,115,135 | 12/1963 | Sarnoff | 604/232 |
| 3,348,545 | 10/1967 | Sarnoff et al. | 604/235 |
| 4,664,653 | 5/1987 | Sagstetter et al. | 604/197 |
| 4,808,169 | 2/1989 | Haber et al. | 604/195 |
| 4,826,489 | 5/1989 | Haber et al. | 604/195 |
| 4,834,717 | 5/1989 | Haber et al. | 604/193 |
| 4,906,231 | 3/1990 | Young | 604/110 |
| 4,909,794 | 3/1990 | Haber et al. | 604/195 |
| 4,931,040 | 6/1990 | Haber et al. | 604/110 |
| 4,935,014 | 6/1990 | Haber | 604/195 |
| 4,957,490 | 9/1990 | Byrne et al. | 604/197 |

FOREIGN PATENT DOCUMENTS

| | | | |
|---|---|---|---|
| 2004734 | 8/1971 | Fed. Rep. of Germany | 604/235 |
| 191676 | 9/1937 | Switzerland | 604/232 |
| 860997 | 2/1961 | United Kingdom | 604/218 |

Primary Examiner—John D. Yasko
Assistant Examiner—Mark O. Polutta
Attorney, Agent, or Firm—Hawes & Fischer

[57] ABSTRACT

A resuable safety module-activator reshielding tool having a barrel within which to receive a single use, disposable, needle/medication cartridge from which a pre-filled supply of fluid medication is injected. The cartridge includes a needle cannula that is advanced outwardly of the barrel to administer an injection and retracted inwardly of the barrel at the conclusion of the injection. The cannula is crushed, shielded and discarded all within the cartridge so as to permit a safe handling thereof after use and avoid an accidental needle stick. The activator tool cannot be reused until the injection has been completed, the cannula destroyed and shielded, and the cartridge removed from the barrel for disposal.

17 Claims, 5 Drawing Sheets

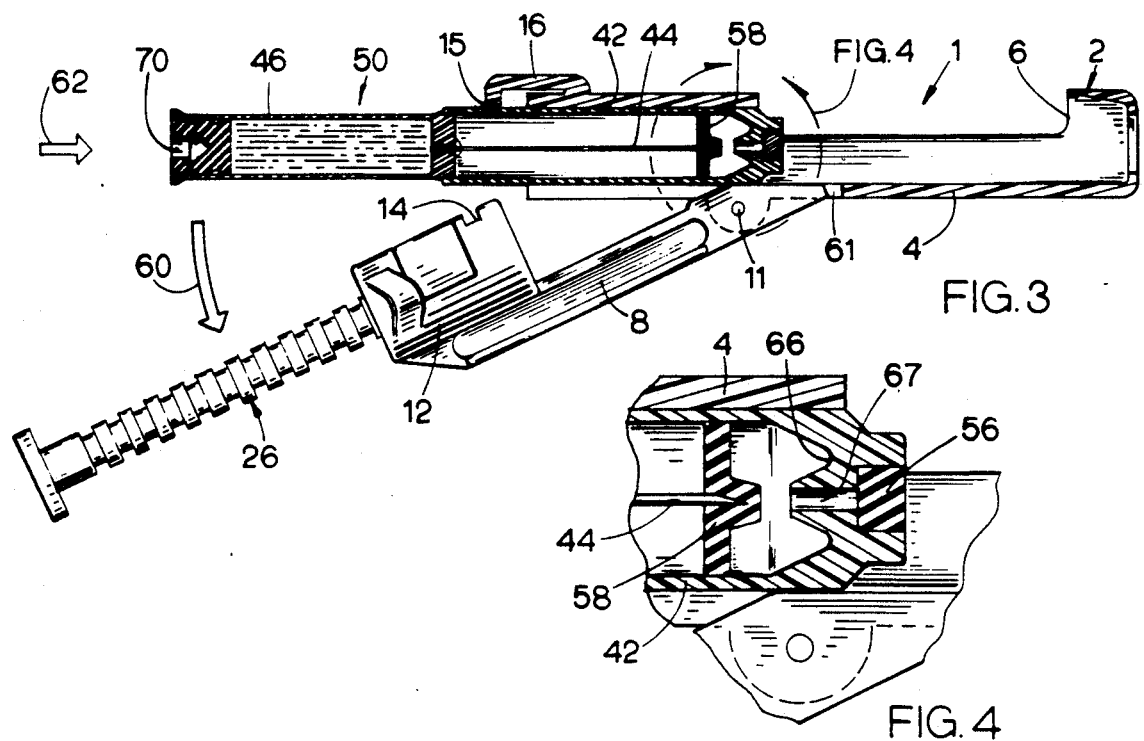
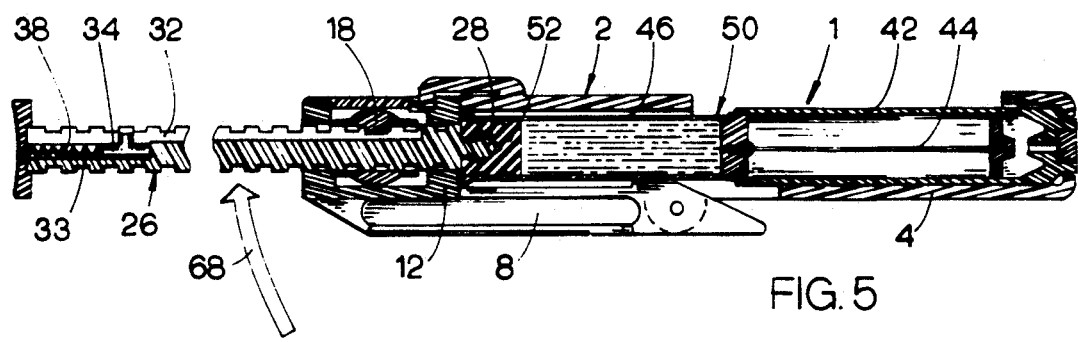
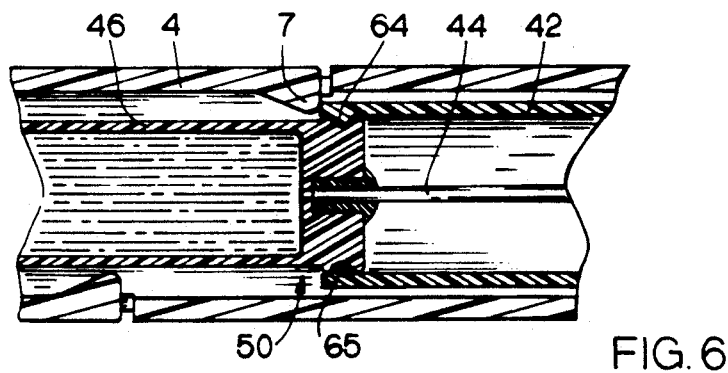

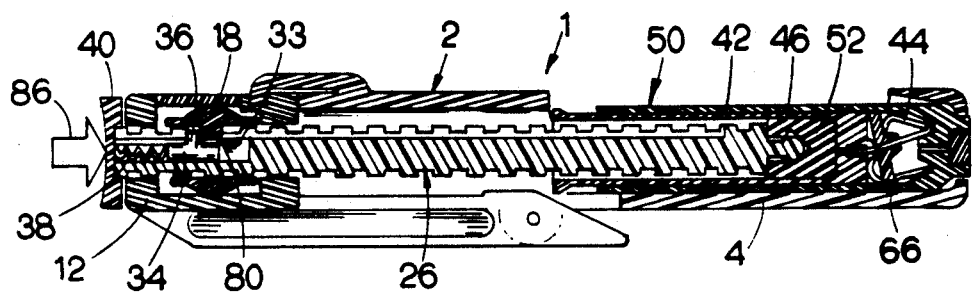
FIG.14
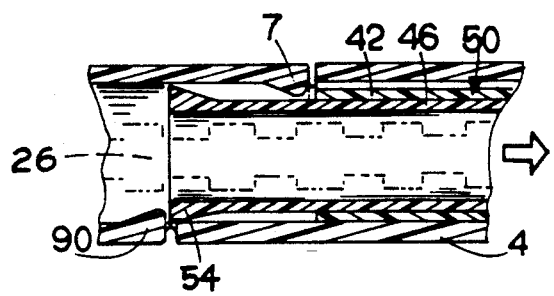
FIG.15
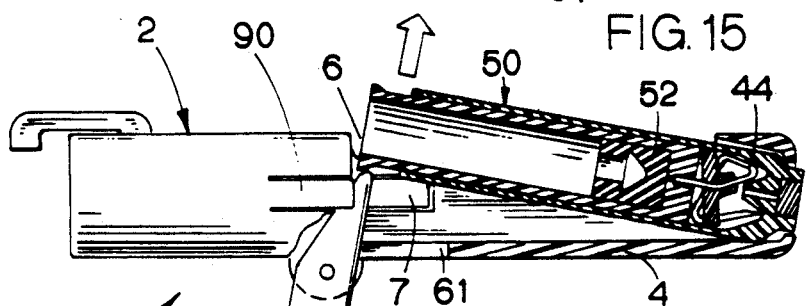
FIG.16
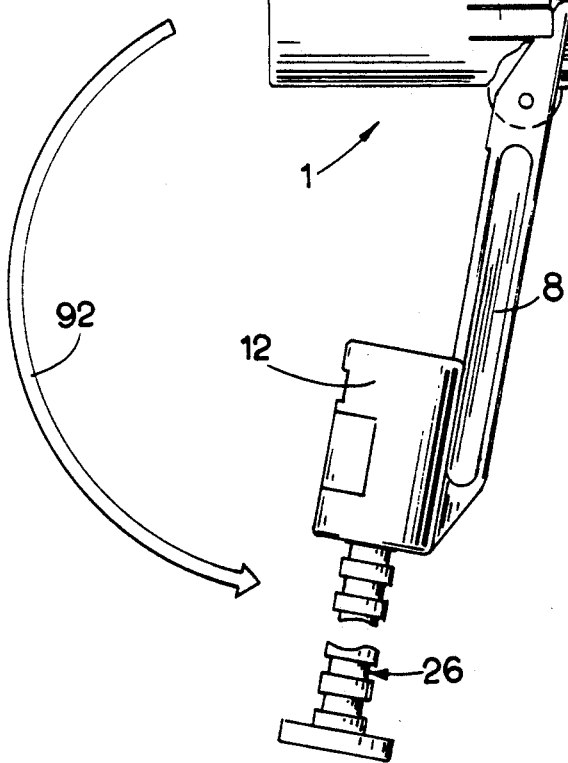

SAFETY MODULE-ACTIVATOR RESHIELDING TOOL

BACKGROUND OF THE INVENTION

1. Field of the Invention

This invention relates to a reusable, safety module-activator reshielding tool that is adapted to receive a disposable, single use, needle/medication cartridge from which a fluid medication can be injected and within which a needle cannula can be retracted, destroyed and shielded upon completion of the injection so that the cartridge can be safely removed from the tool and discarded while preventing reuse of the cannula and avoiding an accidental needle stick and the possible spread of infectious disease.

2. Background Art

Drug abusers are known to share the same hypodermic needle cannula. Moreover, in developing, third world countries, the lack of adequate supplies of medicine and syringes may cause the same syringe to be used to administer successive injections to one patient and then another. In such cases, the reuse of a needle cannula will pose a serious risk of transmitting infectious disease among common users.

Therefore, it would be desirable to have available a means by which an injection of fluid medication can be efficiently administered while fluid aspiration and reuse of the same needle cannula for inoculating different patients can be reliably prevented. It would also be desirable to ensure a destruction of the needle cannula after use to prevent the removal and reuse thereof. It would be further desirable to shield the cannula to permit the safe handling and disposal thereof so as to avoid an accidental needle stick among health care workers and patients to thereby reduce the risk of transmitting infectious disease.

The following U.S. Patent, which have been or will be assigned to the assignee of this patent application, describe a syringe apparatus for receiving a prefilled medication cartridge into which a needle cannula is retracted and shielded after use:

U.S. Pat. No. 4,931,040 issued June 5, 1990
U.S. Pat. No. 4,909,794 issued Mar. 20, 1990
U.S. Pat. No. 4,919,657 issued Apr. 24, 1990
U.S. Pat. No. 4,826,489 issued May 2, 1989.

SUMMARY OF THE INVENTION

In general terms, a reusable safety tool is disclosed for administering an injection of fluid medication from a pre-filled single use needle/medication cartridge. The cartridge includes a medication module containing a supply of fluid medication to be injected, a needle cannula extending from one end of the medication module and a piston located at the opposite end thereof. The cartridge also includes a hollow needle module that surrounds and shields the cannula of the medication module. The needle module is axially aligned with and connected to the medication module and dimensioned so as to permit the medication module to slide reciprocally therethrough.

The safety tool includes a barrel having open proximal and distal ends and a longitudinally extending window formed through a side thereof. The needle/medication cartridge is loaded through the open proximal end of the barrel and slidable distally therethrough. A sleeve housing is connected to a pivot member and rotatable relative to the barrel so as to close the open proximal end thereof and prevent an inadvertent removal of the cartridge. The pivot member is rotatable through an opening in the barrel after an injection has been completed and the needle cannula rendered non-reusable to automatically eject the cartridge through the window of the barrel so that said barrel is empty and ready to receive a new cartridge.

The safety tool also includes a piston stem that is connected to the piston of the medication module and moved distally through the barrel to cause said medication module to slide distally through the needle module and the needle cannula to be advanced outwardly through the open distal end of said barrel. The piston stem also drives the piston through the medication module for expulsing the contents thereof via the cannula. After the injection has been completed, the piston stem is moved proximally through the barrel to slide the medication module proximally through the needle module to retract the cannula inwardly of the barrel to be reshielded within said needle module. A subsequent distal movement of the piston stem through the barrel advances the cannula into contact with a shielded distal end wall of the needle module, such that the cannula is destroyed and rendered non-reusable.

A direction control sleeve is located within the sleeve housing at the proximal end of the barrel to receive the piston stem therethrough. The sleeve cooperates with a pair of flexible leaf springs and a series of axially spaced direction control grooves that are formed in the piston stem to control the movement of said stem through said barrel, such that the movement of the piston stem proximally through said barrel is blocked until the stem is moved distally and completely through said barrel, and the movement of the stem distally through the barrel is blocked until said stem is moved proximally and completely through said barrel.

BRIEF DESCRIPTION OF THE DRAWINGS

FIG. 3 shows the needle/medication cartridge loaded into the barrel of the safety activator tool;

FIG. 4 is an enlarged detail taken from FIG. 3;

FIG. 5 shows the cartridge moved distally through the barrel of the safety activator tool so that an injection can be administered;

FIG. 6 illustrates the axial alignment and interconnection of a needle module and a medication module of the needle/medication cartridge retained within the barrel of the safety activator tool prior to the administration of an injection;

FIG. 14 shows the needle/medication cartridge within the barrel of the safety activator tool after the needle cannula has been collapsed and destroyed therewithin to prevent reuse;

FIG. 15 shows a portion of the needle/medication cartridge that is retained within the barrel of the safety activator tool after the injection has been completed and the medication module has been moved through the needle module to destroy the needle cannula; and FIG. 16 shows the needle/medication cartridge ejected from the barrel of the safety activator tool after the injection has been completed and the cannula has been retracted, destroyed and shielded within the cartridge.

DESCRIPTION OF THE PREFERRED EMBODIMENT

Figure 1:
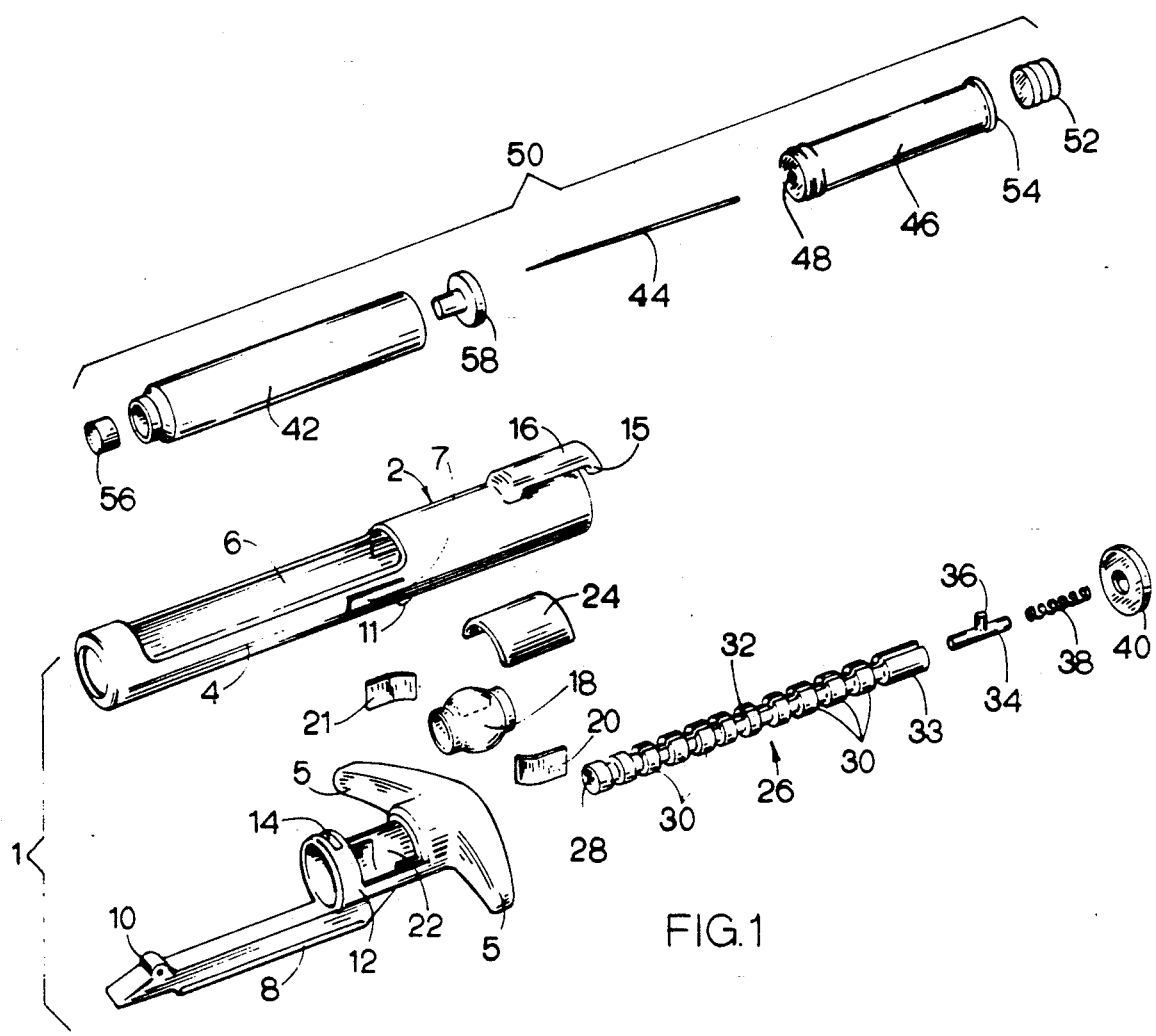
FIG. 1 shows exploded views of the safety activator tool of the present invention and the fluid filled, needle/medication cartridge that is to be received therewithin.
Figure 2:
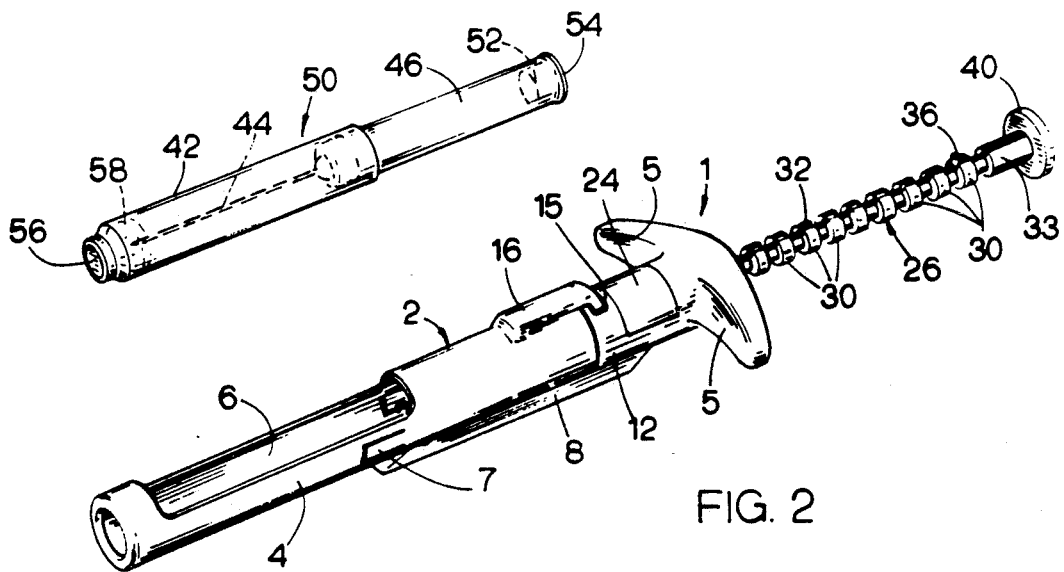
FIG. 2 shows the safety activator tool and the cartridge of FIG. 1 in their respective assembled configurations.

The safety module-activator reshielding tool 1 and the needle/medication cartridge 50 which form the present invention are described while referring to the drawings, where FIG. 1 is an exploded view of tool 1 and cartridge 50, and FIG. 2 shows said tool and cartridge in their assembled configuration. The tool 1 includes an injection molded plastic cartridge activator 2 having a hollow, open ended barrel 4 into which is loaded the soon to be described needle/medication cartridge 50. A pair of oppositely extending finger ledges 5 are coextensively formed with and project outwardly from the proximal end of barrel 4. A longitudinally extending window 6 is formed through the top of barrel 4 to permit both a visual inspection of the cartridge 50 that is loaded therewithin and an ejection of such cartridge at the conclusion of an injection. A needle module catch 7, having a spring-like memory, is integrally and pivotally attached to barrel 4 and located within a recess that is formed in one side of said barrel. A medication module catch (designated 90 in FIGS. 15 and 16), having a spring-like memory, is also integrally and pivotally attached to barrel 4 and located within a recess at the opposite side of said barrel.

Pivotally connected to the barrel 4 of cartridge activator 2 is a longitudinally extending bridge 8. At the forward end of the bridge 8 is a pivot point 10 which is mated to and retained by a corresponding pivot surface 11 at the bottom of barrel 4 so that, in the assembled tool configuration of FIG. 2, the bridge 8 is adapted to be rotated around pivot surface 11 from a first position, at which the bridge engages and supports the barrel 4 thereupon, to a second position, at which a bridge is rotated downwardly and away from the barrel 4 (as shown in FIG. 3). The advantage of permitting bridge 8 to rotate relative to barrel 4 will be described in greater detail hereinafter.

Coextensively formed with bridge 8 at the rear end thereof is a hollow, cylindrical open ended sleeve housing 12. In the assembled tool configuration of FIG. 2, with the bridge 8 in supporting engagement of the barrel 4, the open forward end of sleeve housing 12 is positioned by bridge 8 opposite to and axially aligned with the open proximal end of barrel 4. A latch opening 14 is formed in sleeve housing 12 behind the open forward end thereof so as to releasably receive and retain a tongue 15 from a latch 16 that extends from barrel 4. In this manner, the barrel 4 and the sleeve housing 12 of cartridge activator 2 may be maintained in axial alignment with one another while reliably preventing an inadvertent rotation of the bridge 8 relative to said barrel.

A hollow, generally spherical direction control sleeve 18 and a pair of flexible (e.g. metallic) leaf springs 20 and 21 are located within the sleeve housing 12 through an open window 22 thereof such that the sleeve 18 is concentrically aligned with barrel 4. Sleeve 18 is sized to receive a soon to be described piston stem 26 through the hollow interior thereof. In the assembled tool configuration of FIG. 2, the window 22 of sleeve housing 12 is closed by a sleeve cover 24. The respective functions and cooperation of direction control sleeve 18 and leaf springs 20 and 21 with one another and with the piston stem 26 at the interior of sleeve housing 12 will be described in greater detail hereinafter.

A unidirectional piston stem 26 is provided to be interconnected with the cartridge 50 within the barrel 4 of cartridge activator 2. More particularly, the stem 26 is received within the sleeve housing 12 and adapted to move reciprocally, but in only one direction at a time, through the interior of direction control sleeve 18 and barrel 4. A terminal or tip 28 projects from the forward end of stem 26 to be connected to and control the movement of a piston 52 of a cartridge 50 that has been loaded into the barrel 4. Piston stem 26 has a plurality of axially spaced and circumferentially aligned direction control grooves 30 and a longitudinally extending guide channel 32 formed therein to control the direction in which said stem is moved through the sleeve 18 and barrel 4. The rearward end of piston stem 26 contains a hollow compartment 33 (best shown in FIG. 5) in which to receive a narrow position limiting pin 34 therewithin. Pin 34 has a sleeve control member 36 projecting outwardly and perpendicularly therefrom to be located within the guide channel 32 of stem 26. Position limiting pin is biased forwardly within the compartment 33 of piston stem 26 by a small compression spring 38 that is loaded into said compartment behind the pin 34. The hollow compartment 33 of piston stem 26 is closed by a disk-like thumb cap 40 which prevents removal of the position limiting pin 34 and spring 38 and preserves the bias of said pin towards the forward end of said compartment.

The needle/medication cartridge 50 that is to be loaded into and actuated by activator 2 includes a cylindrical needle module 42, in which a hypodermic needle cannula 44 having a sharpened distal tip is prepackaged and shielded, and a cylindrical medication module 46, which is pre-filled with a fluid medication that is to be expulsed therefrom via cannula 44. The distal end of medication module 46 has an opening 48 formed therein, and the needle cannula 44 is affixed (e.g. bonded or molded) to said distal end so as to communicate with the fluid contents of medication module 46 via opening 48. The cannula 44 is prestressed so as to have a normally canted alignment relative to the longitudinal axes of needle module 42 and barrel 4 for an important purpose that will soon be described. An elastomeric piston 52 is received at the proximal end of medication module 46 to be moved reciprocally therethrough (by means of the piston stem 26). A peripheral locking lip 54 surrounds the proximal end of medication module 46.

The distal end of needle module 42 is tapered so as to receive a needle penetrable sterility seal 56 therewithin. The diameter of needle module 42 is sized so as to be slightly larger than the diameter of medication module 46 to thereby permit module 46 to be received in the proximal end of and slidable through module 42. As is best shown in FIG. 6, a peripheral lip 64 that is formed around the proximal end of needle module 42 is removably received within a peripheral groove 65 that is formed around the distal end of medication module 46, such that in the configuration of FIG. 2, the needle module 42 and medication module 46 are releasably attached together to form the needle/medication cartridge 50 that is suitable to be packaged and transported as a single unit ready for loading into the activator 2 of safety tool 1 with the cannula 44 shielded by needle module 42 and communicating with medication module 46. An elastomeric needle centering device 58 is located within needle module 42 in frictional engagement with the side walls thereof so as to receive the distal tip of cannula 44 and thereby retain the normally canted cannula 44 in coaxial alignment with the longitudinal axes of needle module 42 and the barrel 4 of cartridge activator 2 and thereby permit said cannula to be advanced outwardly of barrel 4 during the administration of an injection.

Referring now to FIG. 3 of the drawings, the needle/medication cartridge 50 is shown being loaded into the barrel 4 of the cartridge activator 2 of safety tool 1. To this end, the bridge 8, to which the sleeve housing 12 is connected, is rotated relative to barrel 4 to permit said cartridge 50 to be loaded through the open proximal end of the barrel. That is, the barrel 4 is grasped with one hand and a downward pulling force is exerted upon bridge 8 with the other hand, so as to move the latch opening 14 in sleeve housing 12 out of contact with the tongue 15 of latch 16 and permit the bridge to rotate (in the direction of the reference arrow 60) around the pivot surface 11 of barrel 4 to thereby move sleeve housing 12 out of axial alignment with said barrel. An opening 61 is formed through the bottom of barrel 4 opposite window 6 to accommodate the forward end of the bridge 8 during the downward rotation thereof, in the manner just described. The cartridge 50 may then be pushed distally (in the direction of reference arrow 62) through the open proximal end of barrel 4 until the distal end of needle module 42 is located adjacent the open distal end of barrel 4 (best shown in FIG. 5).

As previously disclosed when referring to FIGS. 1 and 2, the needle cannula 44 is pre-stressed so as to have a normally canted alignment within the needle module 42. However, the receipt of the distal tip of cannula 44 by needle centering device 58 maintains said cannula in coaxial alignment with module 42 and barrel 4 so that the cannula can be advanced through module 42 and outwardly of barrel 4 to administer an injection (best shown in FIG. 7). As is illustrated in the enlarged detail of FIG. 4, the cannula 44 is retained by needle centering device 58 such that the sharp distal tip of the cannula is aligned with and spaced axially from a narrow bore 67 which is formed through the distal end of needle module 42. The sterility seal 56 is glued across the distal end of said needle module 42 so as to isolate distal bore 67 from the atmosphere and thereby preserve the sterility of cannula 44. The needle module 42 is preferably formed form a relatively hard plastic or glass material, and the distal end thereof is molded to include the bore 67 and a cavity within which to receive the sterility seal 56. The distal end of needle module 42 is molded to also include an annular shielding groove 66 formed around the inner periphery thereof. The distal end of needle module 42 at which the annular shielding groove 66 is located is relatively thick so as to be able to withstand a penetration by cannula 44 for an advantage that will be disclosed in greater detail when referring to FIG. 14.

FIG. 5 of the drawings shows the cartridge activator 2 of safety tool 1 after the needle/medication cartridge 50 has been loaded into and moved distally through the barrel 4 of said activator 2. As the cartridge 50 moves distally through the barrel 4 of cartridge activator 2, and referring briefly to FIG. 6, the spring-like needle module catch 7, that is located within a recess at one side of barrel 4, engages the needle/medication cartridge 50 to prevent a proximal relocation and premature removal of said cartridge from the barrel. More particularly, the catch 7 is initially rotated outwardly of its recess in barrel 4 by the distal movement of the relatively large diameter needle module 42. As soon as needle module 42 is moved past catch 7, the normal spring bias thereof causes said catch to rotate inwardly through its recess and towards the relatively narrow diameter medication module 46. The location of needle module catch 7 at the intersection of the wide needle module 42 and the narrow medication module 46 blocks the proximal relocation of needle module 42 through barrel 4, whereby said needle module is retained at the distal end of the barrel so that an injection can be reliably administered.

Referring once again to FIG. 5, the needle/medication cartridge 50 is shown advanced distally through the barrel 4 of cartridge activator 2 to the ready configuration of tool 1 so as to permit the fluid contents of medication cartridge 46 to be injected via the cannula 44 of needle module 42. After the cartridge 50 is advanced through barrel 4 to the position shown, the connecting bridge 8 is rotated upwardly relative to barrel 4 (in the direction of reference arrow 68) to move the sleeve housing 12 back into axial alignment with the proximal end of said barrel and the cartridge 50 contained therewithin. Accordingly, the tip 28 of piston stem 26 is mated to the piston 52 at a receptacle (designated 70 in FIG. 3) formed therein so that a piston assembly, comprising piston 52 and stem 26, is coupled to the medication module 46 through the hollow direction control sleeve 18 at the interior of sleeve housing 12.

Figure 7:
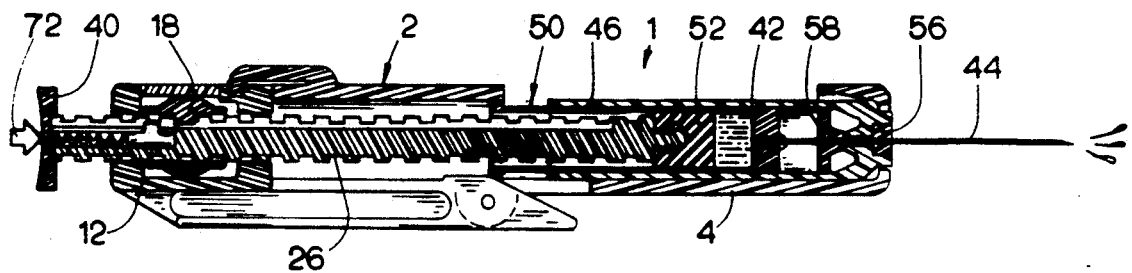
FIG. 7 shows a needle cannula extending outwardly from the barrel of the safety activator tool so that fluid can be expulsed from the needle/medication cartridge via the cannula during the administration of an injection.

FIG. 7 of the drawings shows the safety tool 1 during an injection, such that the fluid contents of needle/medication cartridge 50 are expulsed from the medication module 46 by way of cannula 44. More particularly, a distal pushing force is applied (in the direction of reference arrow 72) to the thumb cap 40 of piston stem 26 to advance said stem through direction control sleeve 18. This pushing force is transferred by way of stem 26 to piston 52 at the proximal end of cartridge 50 which, in turn, causes a hydraulic pressure to be generated which overcomes the attachment of the modules 42 and 46 at lip 64 and groove 65 (of FIG. 6) and drives the relatively small diameter medication module 46 distally through the relatively large diameter needle module 42 until the cannula 44, which is bonded to medication module 46, is correspondingly forced through the sterility seal 56 and moved to an axially extended position relative to the barrel 4 of activator 2. With the medication module 46 advanced through needle module 42 and cannula 44 moved outwardly of barrel 4, the continued application of force to the thumb cap 40 of piston stem 26 will cause piston 52 to be driven distally through medication module 46, whereby to inject the fluid contents thereof via said cannula.

As an important advantage of the present invention, the piston stem 26 cooperates with the direction control sleeve 18 within sleeve housing 12 during the administration of an injection to allow fluid expulsion but prevent fluid aspiration. That is to say, and referring concurrently to FIGS. 8 and 9 of the drawings, by virtue of the direction control grooves 30 of piston stem 26 and the leaf springs 20 and 21 of direction control sleeve 18, the piston stem moves unidirectionally in barrel 4 (i.e. to be advanced through direction control sleeve 18 in the distal direction only) during the administration of an injection, such that the proximal withdrawal of stem 26 through barrel 4 and sleeve 18 is blocked until the injection has been completed and piston stem 26 has been moved to its distal-most position in barrel 4.

Figure 9:
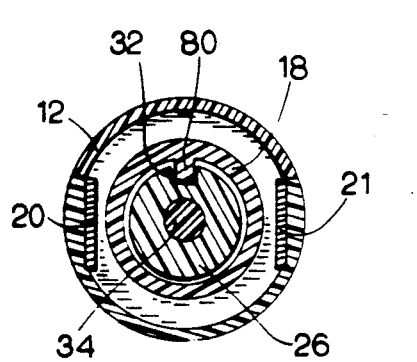
FIGS. 8-11 and 13 are cross-sections through a sleeve housing of the barrel of the safety activator tool in which a direction control sleeve cooperates with and is moved by a piston stem to control the direction in which said piston stem is moved through said barrel.
Figure 8:
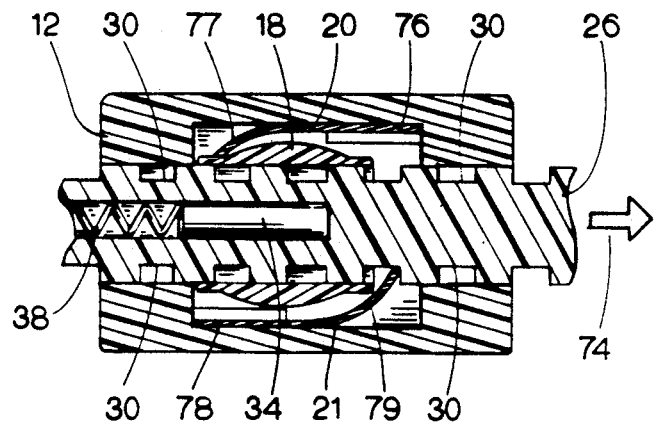

FIGS. 8 and 9 of the drawings show the relationship of the flexible leaf springs 20 and 21 of direction control sleeve 18 to the position control grooves 30 of piston stem 26 during the time when piston stem 26 is advanced distally through the hollow interior of sleeve 18 (in the direction of the reference arrow 74) for the purpose of administering an injection and expulsing fluid medication from the medication module 46 of needle/medication cartridge 50 in the manner described while referring to FIG. 7. More particularly, each leaf spring 20 and 21 has a respective fixed end 76 and 78 and a respective free end 77 and 79. Leaf springs 20 and 21 are located within sleeve housing 12 at opposite sides of piston stem 26, and the fixed ends 76 and 78 of said springs 20 and 21 are secured to diagonally opposite walls of sleeve housing 12.

In the spring alignment shown in FIGS. 8 and 9, where piston stem 26 is to be moved distally through the interior of direction control sleeve 18 so that an injection can be administered, the free end 77 of one leaf spring 20 rests atop the sleeve 18, while the free end 79 of the other spring 21 is received within one of the circumferential direction control grooves 30 of stem 26. Hence, it may be appreciated that the free end 77 of spring 20 is held, by sleeve 18, out of receipt by the direction control grooves 30 so as not to impede the distal advancement of piston stem 26 through said sleeve 18. However, the free end 79 of leaf spring 21 is received within a direction control groove 30 so as to form a stop therewithin and block the proximal withdrawal of piston stem 26 through sleeve 18 (in a direction opposite that represented by reference arrow 74). Because of the flexible nature thereof, the free end 79 of leaf spring 21 will jump from one direction control groove 30 to the next as piston stem 26 is pushed distally through direction control sleeve 18. However, regardless of the groove 30 in which the free end 79 of spring 21 is received during the distal advancement of piston stem 26, the receipt of such free end in such groove will prevent the proximal withdrawal of the stem 26 through sleeve 18.

The direction control sleeve 18 is adapted to travel axially through sleeve housing 12 and slide with piston stem 26 at the conclusion of the injection to permit stem 26 to move proximally through the interior of direction control sleeve 18. As shown in FIG. 9, the sleeve 18 is provided with a radially and inwardly projecting tooth 80. The tooth 80 is sized to be received within and ride through the longitudinally extending channel 32 that is formed in piston stem 26 (shown in FIG. 5) as said piston stem is advanced distally through direction control sleeve 18. When the piston stem 26 is advanced to its distal-most position in the barrel 4 of cartridge activator 2 to thereby complete an injection (such that the piston 52 is driven through the medication module 46 to expulse the fluid therefrom), the direction control sleeve 18 is slid axially along stem 26 from the position shown in FIG. 8, where the proximal withdrawal of stem 26 is blocked, to a distally advanced position of FIG. 10, where the proximal withdrawal of stem 26 through sleeve 18 will be permitted.

Figure 10:
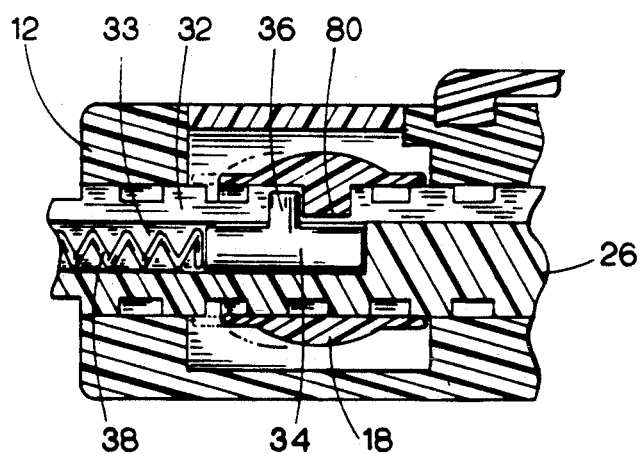

More particularly, and referring to FIG. 10 of the drawings, after piston stem 26 has been advanced to its distal-most position in the barrel 4 of activator 2 at the conclusion of an injection, the spring-biased position limiting pin 34 within the hollow compartment 33 at the rearward end of stem 26 is moved into contact with the tooth 80 of direction control sleeve 18 to displace said sleeve. That is, position limiting pin 34 is carried by piston stem 26, such that the sleeve control member 36 of pin 34, which projects from pin 34 into the longitudinally extending channel 32 of stem 26, is moved into the sleeve housing 12 and into engagement with the tooth 80 which, as previously described, projects radially inward from sleeve 18 into said channel 32. Accordingly, the sleeve control member 36 of position limiting pin 34 pushes the tooth 80 of direction control sleeve 18 axially through channel 32, whereby sleeve 18 is displaced from its initial position of FIG. 8 (shown in phantom in FIG. 10) to a distally advanced position within sleeve housing 12. With the direction control sleeve 18 relocated to the distally advanced position, as shown, the piston stem 26 will be freed from its engagement with leaf spring 21 (of FIG. 8) to permit said stem to be withdrawn proximally through sleeve 18.

Figure 11:
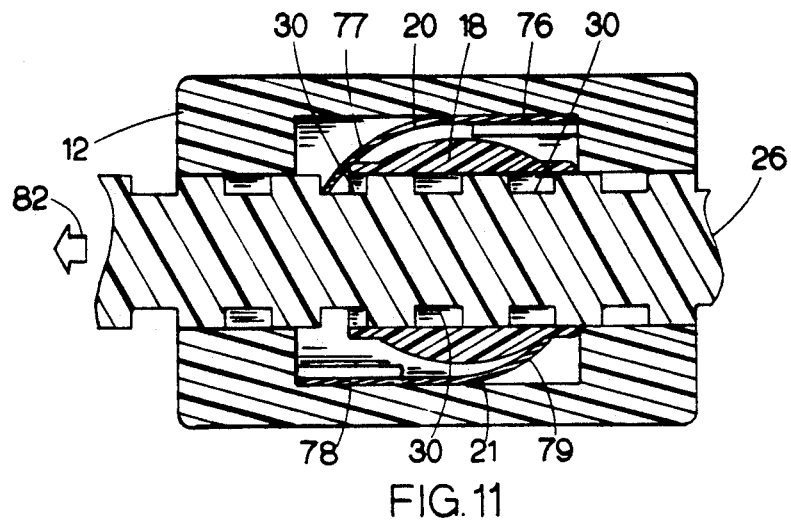

More particularly, and referring to FIG. 11 of the drawings, the distal advancement of direction control sleeve 18 through housing 12 will cause the free end 79 of leaf spring 21 to be lifted out of its previous receipt within one of the circumferential direction control grooves 30 in piston stem 26 (as shown in FIG. 8). That is, by virtue of its spherical configuration, sleeve 18 will slide under the free end 79 of spring 21, such that said free end 79 will be removed from groove 30 to rest atop said sleeve 18 and be held out of receipt by the grooves 30 of piston stem 26. Thus, it may be appreciated that the leaf spring 21 no longer impedes the withdrawal of unidirectional piston stem 26 in a proximal direction through sleeve 18 (in the direction of reference arrow 82). However, with sleeve 18 advanced distally in housing 12 relative to the opposing leaf spring 20, the free end 77 of spring 20 will fall off sleeve 18 and drop into one of the direction control grooves 30 of piston stem 26 so as to form a stop therewithin and block the distal advancement of stem 26 through direction control sleeve 18 (in a direction opposite that represented by reference arrow 82). Hence, piston stem 26 is again movable in only one (i.e. proximal) direction through sleeve 18.

Figure 12:
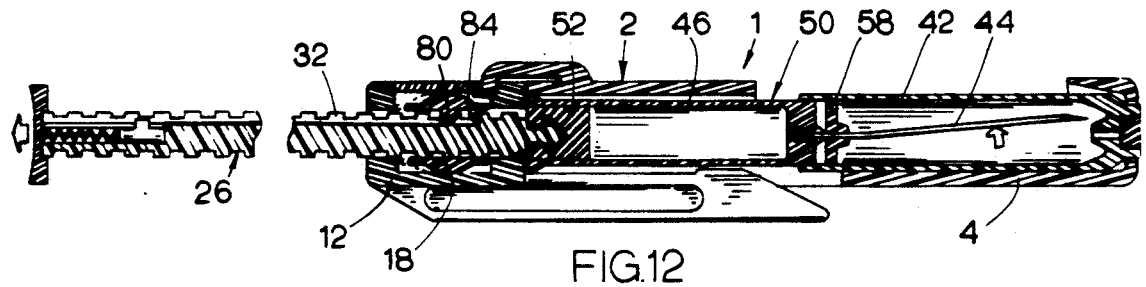
FIG. 12 shows the needle/medication cartridge within the barrel of the safety activator tool after the injection has been completed and the needle cannula has been retracted therewithin.

Accordingly, and as is shown in FIG. 12 of the drawings, a pulling force is applied to piston stem 26 such that said piston stem is withdrawn proximally through direction control sleeve 18. Inasmuch as piston stem 26 is connected to the medication module 46 of needle/medication cartridge 50 at the piston 52 thereof, a proximal withdrawal of stem 26 through sleeve 18 causes a corresponding withdrawal of medication module 46 from needle module 42 since, as previously described when referring to FIG. 6, needle module 42 is retained, by means of the needle module catch 7, at the distal end of the barrel 4 of cartridge activator 2. With medication module 46 pulled proximally and outwardly of needle module 42, the needle cannula 44, which is bonded to an end of said medication module 46, is retracted inwardly of said needle module 42.

As previously described, cannula 44 has a normally canted alignment relative to the longitudinal axes of needle module 42 and barrel 4. Therefore, cannula 44 will now assume such canted alignment within module 42, since the needle centering device 58, which formerly held cannula 44 in coaxial alignment with module 32, will slide rearwardly along said cannula when medication module 46 is moved through needle module 42 during the administration of the injection (shown in FIG. 7).

Figure 13:
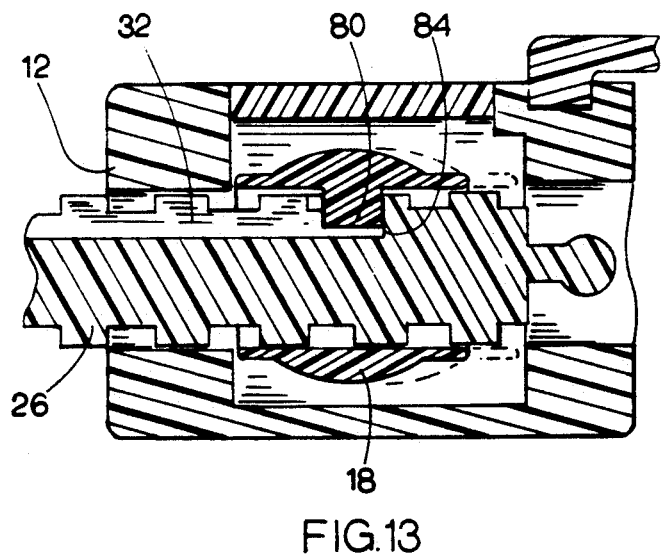

When the unidirectional piston stem 26 is withdrawn to its proximal-most position in barrel 4 and through the direction control sleeve 18 (such that cannula 44 is retracted completely within needle module 42), the sleeve 18 is moved axially along stem 26 from the position shown in FIG. 11, where the distal advancement of stem 26 is blocked, to a proximally relocated position of FIG. 13, where stem 26 may once again be advanced distally through sleeve 18. More particularly, and referring concurrently to FIGS. 12 and 13 of the drawings, when piston stem 26 is withdrawn to its proximal-most position in barrel 4, the distal end wall 84 of the longitudinally extending guide channel 32 of stem 26 is moved into contact with the tooth 80 that projects inwardly from direction control sleeve 18 into said channel 32, whereby to cause said sleeve to be displaced proximally through sleeve housing 12. That is, the end wall 84 of guide channel 32 is moved towards and into engagement with tooth 80 as piston stem 26 is withdrawn proximally through sleeve 18. Accordingly, the end wall 84 pushes the tooth 80, such that sleeve 18 is displaced proximally through sleeve housing 12 from its relatively distal position (shown in phantom in FIG. 13), where the piston stem may be withdrawn proximally through direction control sleeve 18, to a proximally relocated position, at which the proximal withdrawal of stem 26 is blocked. At its proximal-most position in barrel 4, the piston stem 26 is detached from its piston 52 (best illustrated in FIG. 13).

It may be appreciated that the proximally relocated position (as shown in FIG. 13) to which direction control sleeve 18 is moved within sleeve housing 12 when piston stem 26 is withdrawn to its proximal-most position through the barrel 4 of cartridge activator 2 is identical to the initial position of sleeve 18 in housing 12 that was previously disclosed when referring to FIG. 8. Thus, with sleeve 18 returned to the relatively proximal position of FIGS. 8 and 13, the unidirectional piston stem 26 will be freed from its engagement with leaf spring 20 (of FIG. 11) to permit said stem to be once again advanced in a single direction (i.e. distally) through barrel 4 and sleeve 18. Since the cooperation of direction control sleeve 18 and the leaf springs 20 and 21 with piston stem 26 to permit the distal advancement of stem 26 through barrel 4 and sleeve 18, while blocking the proximal withdrawal thereof, was already disclosed in detail, such cooperation will not be presented again.

In FIG. 14 of the drawings, the unidirectional piston stem 26, the advancement of which is now possible in the distal direction while withdrawal in the proximal direction is blocked, is once again pushed distally (at the thumb cap 40 thereof and in the direction of reference arrow 86) through the barrel 4 of cartridge activator 2. The distal pushing force applied to piston stem 26 is transferred to piston 52, whereby the empty medication module 46 and the needle cannula 44 attached thereto are advanced distally through the needle module 42 of needle/medication module 50. Inasmuch as the needle cannula 44 is canted within needle module 42, said cannula is moved towards and into contact with the shielding groove 66 at the distal end of module 42 (as opposed to be being returned to the outwardly extended position relative to barrel 4 at which the injection was administered). Hence, the cannula 44 is axially collapsed and thereby crushed against the needle impenetrable shielding groove 66 of needle module 42 so as to be rendered non-reusable.

After the cannula 44 has been crushed, an additional distal pushing force is applied (in the direction of reference arrow 86) to the thumb cap 40 of piston stem 26 to cause a slight distal advance of stem 26 through the direction control sleeve 18. Such distal pushing force is transferred from thumb cap 40 to needle/medication cartridge 50 by way of piston stem 26 and piston 52 to correspondingly cause cartridge 50 to move a short distance through the barrel 4. It may be noted that the direction control sleeve 18 will be returned to its relatively distal position within sleeve housing 12 (as described when referring to FIG. 11) as piston stem 26 is pushed distally through sleeve 18. Since sleeve 18 is already at the distal end of its housing 12, any attempted further distal relocation of said sleeve through said housing is blocked. Accordingly, the distal pushing force applied to thumb cap 40 also causes an equal and opposite proximal force to be generated by the engagement of the sleeve control member 36 of position limiting pin 34 with the tooth 80 of sleeve 18, whereby to compress the spring 38 between thumb cap 40 and limiting pin 34 within the hollow compartment 33 of piston stem 26. That is to say, pin 34 remains stationery within compartment 33 as piston stem 26 is pushed further through direction control sleeve 18, such that spring 38 is compressed. In other words, the spring 38 facilitates the distal advancement of piston stem 26 without a corresponding distal advancement of direction control sleeve 18.

With needle/medication cartridge 50 pushed by piston stem 26 to its distal/most position within the barrel 4 of cartridge activator 2, and referring now to FIG. 15 of the drawings, said cartridge is interfaced with a spring-like medication module catch 90, such that the proximal withdrawal of cartridge 50 through barrel 4 will be blocked. More particularly, and as was previously discussed when referring to FIGS. 1 and 2, medication module catch 90 is located in a recess formed at one side of barrel 4 and opposite the side of said barrel at which the needle module catch 7 is located. The additional distal advancement of cartridge 50 through barrel 4 (when thumb cap 40 of piston stem 26 is pushed to compress spring 38 of FIG. 14) moves the medication module 46 of cartridge 50 distally and past catch 90. That is, the catch 90 is initially rotated outwardly of its recess in barrel 4 by the distal movement of the peripheral locking lip 54 of medication module 46. As soon as the medication module 46 is moved past catch 90, the normal spring bias thereof causes said catch to rotate inwardly through its recess and behind locking lip 54. The location of medication module catch 90 behind medication module 46 and needle module catch 7 behind needle module 42 retains the needle/medication cartridge 50 at its distal-most position within barrel 4 and prevents any proximal relocation of modules 42 and 46 through said barrel.

With catches 7 and 90 preventing any proximal relocation of the modules 44 and 46 of needle/medication cartridge 50 through barrel 4 of cartridge activator 2, the cartridge 50 is ready to be removed from said barrel for disposal. More particularly, and referring to FIG. 16 of the drawings, the piston stem 26 is free to be pulled to its proximal-most position in barrel 4 so that stem 26 is once again detached from its piston 52. The bridge 8, to which sleeve housing 12 is connected, is rotated downwardly (in the direction of reference arrow 92) relative to barrel 4 in the manner previously described when referring to FIG. 3. Accordingly, the sleeve housing 12 at one end of bridge 8 is moved downwardly and out of axial alignment of barrel, while the opposite end of bridge 8 is moved upwardly through the opening 61 at the bottom of said barrel. The upward movement of bridge 8 through opening 61 serves to automatically eject the needle/medication cartridge 50 from barrel 4 through the longitudinally extending window 6 formed therein. Thus, cartridge 50 may be safely handled and discarded with the needle cannula 44 rendered non-reusable and non-accessible therewithin, such that an accidental needle stick and the spread of contagious infection may be advantageously avoided. What is more, the receive a new needle/medication cartridge 50 in the same manner as described when referring to FIG. 3, so that another injection may be safely administered.

It should now be apparent that needle/medication cartridge 50 is for a single use only. Moreover, the activator tool 1 cannot be reused until cartridge 50 has been removed from barrel 4. However, said cartridge 50 cannot be removed from barrel 4 until the injection has been completed and the needle cannula 44 is destroyed. Inasmuch as piston stem 26 is unidirectional, fluid aspiration is prohibited, such that unauthorized and/or illegal use of the tool 1 is prevented.

While a preferred embodiment of the invention has been shown and described, various modifications and changes may be made without departing from the true spirit and scope of the invention.

Having thus set forth a preferred embodiment of the invention, what is claimed is:

1. An activator tool in which to receive a cartridge having a fluid filled medication module, a piston at one end of the module and a needle cannula projecting outwardly from the opposite end of the module and communicating with the interior thereof so that fluid can be injected from said module, said activator tool comprising:
    a hollow barrel including an open proximal end through which to receive the cartridge and an open distal end through which the needle cannula of the cartridge extends for administering an injection after the cartridge is received in and moved distally through said barrel;
    an open window extending longitudinally through said barrel between the proximal and distal ends thereof;
    means for injecting the fluid of said medication module via the cannula;
    means for retracting the needle cannula inwardly of said barrel and completely within said cartridge to be shielded thereby at the conclusion of the injection; and
    means for ejecting said cartridge through the window of said barrel after the injection has been completed and the cannula has been retracted within said cartridge.

2. The activator tool recited in claim 1, further comprising closure means removably positioned across the open proximal end of said barrel to prevent the cartridge from being removed therethrough after said cartridge has been received within and moved distally through said barrel.

3. The activator tool recited in claim 2, further comprising pivot surface means, one end of said pivot surface means connected to said closure means and the opposite end thereof pivotally connected to said barrel, such that said pivot surface means is rotatable relative to said barrel to remove said closure means from the proximal end thereof.

4. The activator tool recited in claim 3, further comprising an opening formed through said barrel and located opposite said longitudinally extending window, the pivotally connected end of said pivot surface means being rotatable through said opening and into said barrel to eject the cartridge through said window.

5. The activator tool recited in claim 1, wherein said cartridge also has a hollow needle module axially aligned with and connected to the medication module to surround and shield the needle cannula thereof and sized to permit the medication module to be moved reciprocally therethrough,
    said tool further comprising a piston stem to be connected to the piston of said medication module and moved distally through said barrel to cause said medication module to be moved distally through said needle module to thereby advance the needle cannula outwardly of said barrel through the open distal end thereof and to drive the piston through said medication module for injecting the fluid thereof via the cannula, and
    said piston stem being movable proximally through said barrel after the injection has been completed to move said medication module proximally through said needle module for retracting the needle cannula inwardly of said barrel to be retracted and reshielded within said needle module.

6. The activator tool recited in claim 5, further comprising first catch means extending inwardly from said barrel to engage said needle module and prevent the proximal relocation thereof through said barrel after said cartridge has been received in and moved distally through said barrel.

7. The activator tool recited in claim 6, further comprising second catch means extending inwardly from said barrel to engage said medication module and prevent the proximal relocation thereof through said barrel after the injection has been completed and said piston stem has first moved said medication module proximally through said needle module to retract the needle cannula therewithin and then returned said medication module distally through said needle module and to its distal-most location within said barrel, the needle cannula having a normally canted alignment relative to the longitudinal axis of the needle module and said needle module having a shielded distal end wall, such that the canted cannula is moved into contact with and collapsed against the shielded distal end wall of said needle module when said piston stem returns said medication module distally through said needle module.

8. The activator tool recited in claim 5, further comprising means cooperating with said piston stem to control the distal and proximal movements of said stem through said barrel, such that the movement of said stem proximally through said barrel is blocked until said stem is moved distally and completely through said barrel, and the movement of said stem distally through said barrel is blocked until said stem is moved proximally and completely through said barrel.

9. Apparatus for administering an injection, comprising:
   a cartridge including:
      a medication module containing a supply of fluid medication, a needle cannula extending from a distal end of said medication module and communicating with the fluid supply therewithin, and a piston located at the proximal end of said module, and
      a hollow needle module surrounding and shielding the cannula of said medication module and axially aligned with and connected to said medication module, said needle module being dimensioned relative to said medication module to permit said medication module to slide reciprocally therethrough; and
   an activator tool including:
      a barrel having distal and proximal ends and receiving said cartridge therewithin, and
      a piston stem to be connected to the piston of said medication module and moved distally through said barrel to cause said medication module to slide distally through said needle module and thereby advance the needle cannula outwardly of said barrel through an opening in the distal end thereof and to drive said piston distally through said medication module for injecting the fluid thereof via said cannula, said piston stem moved proximally through said barrel after the injection has been completed to slide said medication module proximally through said needle module for retracting said cannula inwardly of said barrel to be reshielded within said needle module.

10. The apparatus recited in claim 9, wherein said needle module has a shielded distal end wall with an opening formed therein through which the needle cannula is advanced and retracted when said medication module is slid by said piston stem through said needle module, said cannula having a canted alignment within said needle module, such that a subsequent distal movement of said piston stem through said barrel after said cannula has been retracted proximally and inwardly thereof slides said medication module through said needle module and moves said canted cannula into contact with the shielded distal end wall of said needle module to collapse and thereby destroy said cannula, whereby to prevent a reuse thereof.

11. The apparatus recited in claim 10, said activator tool further including means by which to eject said cartridge from said barrel with said medication module received within said needle module and said needle cannula destroyed and shielded by said needle module.

12. The apparatus recited in claim 9, said activator tool further including means to engage said piston stem to control the distal and proximal movements of said stem through said barrel, such that the movement of said stem proximally through said barrel is blocked until said stem is moved distally and completely through said barrel, and the movement of said stem distally through said barrel is blocked until said stem is moved proximally and completely through said barrel.

13. Apparatus for administering an injection of fluid including a fluid filled cartridge having a needle cannula projecting from one end thereof and a piston located at the opposite end, said apparatus also including:
   a hollow barrel having open proximal and distal ends and adapted to receive said cartridge therewithin such that the needle cannula of said cartridge extends outwardly from said open distal end for administering the injection;
   a piston stem attached to the piston of said cartridge through the open proximal end of said barrel and movable reciprocally thorough said barrel, said piston stem being moved distally through said barrel to correspondingly move said piston through said cartridge to expulse fluid therefrom via the cannula, and said piston stem being moved proximally through said barrel at the conclusion of the injection to cause the cannula to be retracted inwardly of said barrel for receipt within said cartridge; and
   direction control means engaging said piston stem to control the distal and proximal movements of said piston stem through said barrel, such that a proximal movement of said piston stem through said barrel is blocked while said stem is moved distally through said barrel to expulse the fluid contents of said cartridge, and a distal movement of said piston stem through said barrel is blocked while said stem is moved proximally through said barrel to retract the cannula within said cartridge.

14. The apparatus recited in claim 13, wherein said piston stem has a series of axially spaced grooves formed therein and said direction control means includes projection means to be received within at least one of said grooves and movable to successive grooves of said piston stem as said stem is moved through said barrel relative to said projection means, the receipt of said projection means within the grooves of said piston stem permitting the distal movement but blocking the proximal movement of said stem through said barrel and permitting the proximal movement but blocking the distal movement of said stem through said barrel.

15. The apparatus recited in claim 14, wherein the projection means of said direction control means includes a pair of oppositely projecting direction control fingers, one or the other of said fingers being received within the grooves of said piston stem depending upon whether said stem is moved distally or proximally through said barrel, one of said direction control fingers projecting in a first direction for receipt within said grooves to permit distal but block proximal movement of said piston stem through said barrel and the second of said direction control fingers projecting in an opposite direction to said first finger for receipt within said grooves to permit proximal but block distal movement of said piston stem through said barrel.

16. The apparatus recited in claim 15, wherein said direction control means also includes a sleeve through which said piston stem is movable during the distal and proximal movements of said stem through said barrel, said sleeve being moved by said stem between said first and second direction control fingers to position one or the other of said fingers within the grooves of said piston stem depending upon the distal or proximal direction in which said stem is moving through said barrel.

17. The apparatus recited in claim 16, wherein said piston stem has a longitudinally extending channel formed therein, a first sleeve control surface formed at one end of said channel and a second sleeve control surface formed at the opposite end of said channel, said sleeve having a tooth extending into said channel, the first and second sleeve control surfaces of said channel being alternately moved into contact with the tooth of said sleeve as said piston stem moves between its distal-most and proximal-most locations in said barrel for repositioning said sleeve relative to said first and second direction control fingers to thereby move one or the other of said fingers into receipt by the grooves of said piston stem to control the direction in which said stem is moved through said barrel.

* * * * *